Figure 1:
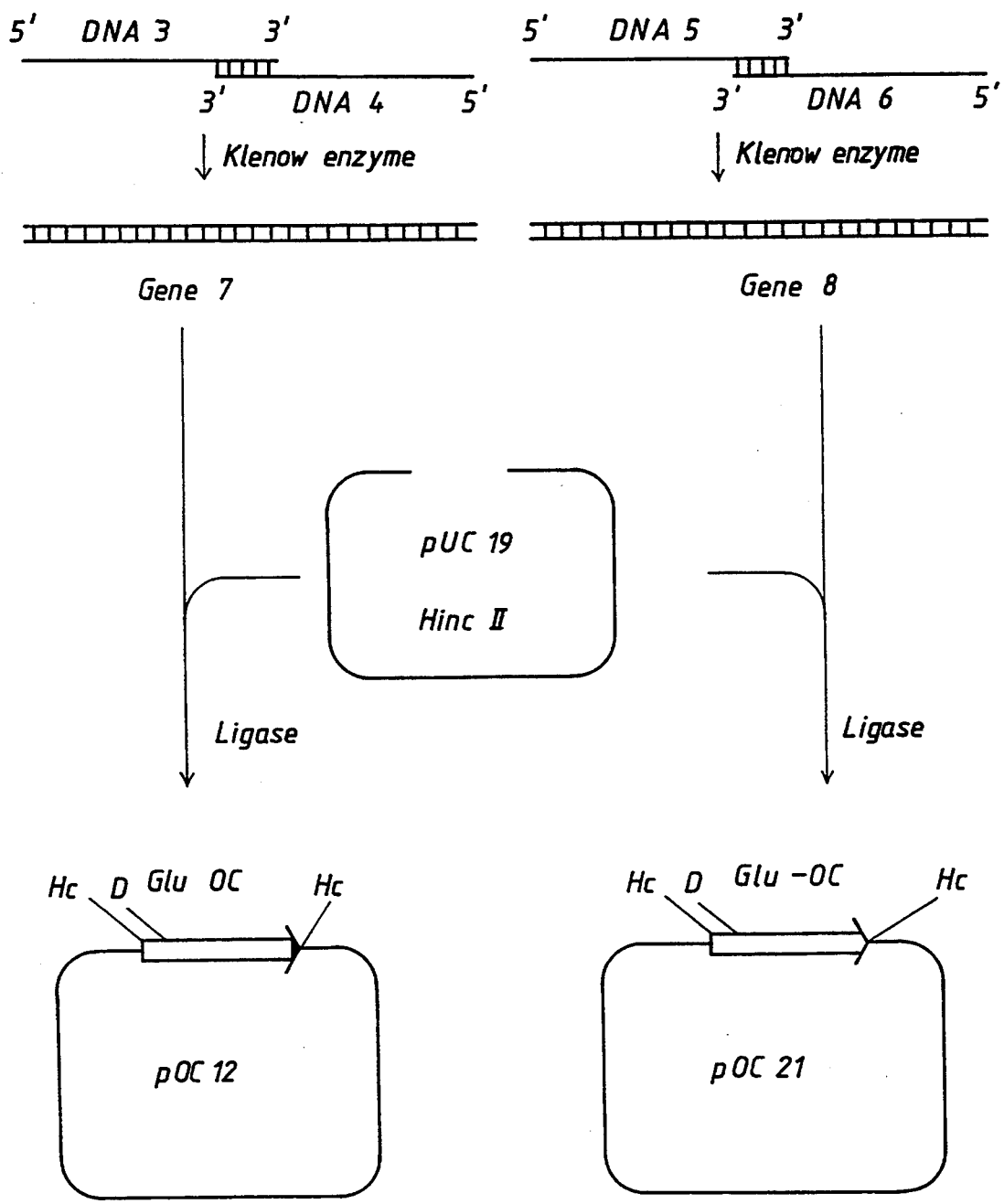

United States Patent [19]

Koyama et al.

[11] Patent Number: 5,434,245
[45] Date of Patent: Jul. 18, 1995

[54] POLYPEPTIDES AND METHOD FOR PREPARING THE SAME

[75] Inventors: Nobuto Koyama, Uji; Fusao Kimizuka, Ohmihachiman; Ikunoshin Kato, Uji, all of Japan

[73] Assignee: Takara Shuzo Co., Ltd., Japan

[21] Appl. No.: 993,980

[22] Filed: Dec. 16, 1992

Related U.S. Application Data

[62] Division of Ser. No. 855,473, Mar. 23, 1992, abandoned, which is a division of Ser. No. 444,786, Dec. 1, 1989, abandoned.

[30] Foreign Application Priority Data

Dec. 6, 1988 [JP] Japan .................. 63-306931
Aug. 22, 1989 [JP] Japan .................. 1-214239

[51] Int. Cl.$^6$ ...................... C07K 14/47; C07K 14/70
[52] U.S. Cl. ..................... 530/324; 435/69.7; 435/69.1
[58] Field of Search ............. 530/324; 435/69.7, 69.1, 435/172.1

[56] References Cited

U.S. PATENT DOCUMENTS

| | | | |
|---|---|---|---|
| 4,438,208 | 3/1984 | Deftos et al. | 436/542 |
| 4,795,804 | 1/1989 | Urist | 530/350 |

OTHER PUBLICATIONS

Poser et al., J. of Biol. Chem., vol. 255 No. 18, pp. 8685–8691, 1980.
Celeste et al., EMBO Journal, vol. 5 No. 8, pp. 1885–1890, 1986.

*Primary Examiner*—Keith C. Furman
*Attorney, Agent, or Firm*—Wenderoth, Lind & Ponack

[57] ABSTRACT

There is provided a polypeptide having the following formula (I'), and which polypeptide is referred to as Glu-OC and a process for the preparation thereof.

```
1    2    3    4    5    6    7    8    9              (I')
Tyr—Leu—Tyr—Gln—Trp—Leu—Gly—Ala—Pro—

10   11   12   13   14   15   16   17   18
Val—Pro—Tyr—Pro—Asp—Pro—Leu—Glu—Pro—

19   20   21   22   23   24   25   26   27
Arg—Arg—Glu—Val—Cys—Glu—Leu—Asu—Pro—

28   29   30   31   32   33   34   35   36
Asp—Cys—Asp—Glu—Leu—Ala—Asp—His—Ile 37   38   39   40   41   42   43   44   45
Gly—Phe—Gln—Glu—Ala—Tyr—Arg—Arg—Phe—

46   47   48   49
Tyr—Gly—Pro—Val
```

1 Claim, 4 Drawing Sheets

POLYPEPTIDES AND METHOD FOR PREPARING THE SAME

This application is a Division of now abandoned application, Ser. No. 07/855,473, filed on Mar. 23, 1992, abandoned, which is a division of now abandoned application Ser. No. 07/444,786 filed on Dec. 1, 1989, abandoned.

This invention relates to a novel polypeptide in which the γ-carboxyglutamate (Gla) residues at the 21-and 24-positions of human osteocalcin are replaced by glutamate (Glu), and to a method for the preparation of said polypeptide. This invention also relates to purified human osteocalcin which does not contain any other substance arising from the body and a method for its preparation.

Osteocalcin (herein after sometimes referred to as OC) is a protein produced in the bone; its binding to calcium is dependent on vitamin K. Osteocalcin seems to act in the process of bone formation as a growth factor for bone. Thus, it may be useful as a drug to treat disorders which arise from abnormalities in bone metabolism.

In the body, osteocalcin is synthesized in bone tissue, mainly by germinal cells of the bone; it is related to bone metabolism, bone calcification, and ectopic calcification, and is connected to metastases of cancer to the bone, Paget's disease syndrome, primary hyperparathyroidism, and osteopenia. Human osteocalcin is a Gla-protein with 49 amino acid residues and with γ-carboxyglutamates at the 21- and 24-positions J. Biol. chem. 255(18) 8685–8691 (1980))

Natural osteocalcin can be extracted from the bones of cattle and the like, but it is difficult to obtain a large amount of purified human osteocalcin. Further, the structures of bovine osteocalcin and human osteocalcin are different.

Human osteocalcin is a polypeptide with a relatively long chain of 49 amino acids, and it is difficult to synthesize the same chemically. To obtain a large amount of human osteocalcin inexpensively, it is necessary to have a large and inexpensive supply of the precursor of human osteocalcin, which is a polypeptide in which the γ-carboxyglutamates at the 21- and 24- positions of human osteocalcin are replaced with glutamate, said polypeptide having the following formula (I') and which substance is hereinafter referred to as Glu-OC.

```
 1    2    3    4    5    6    7    8    9        (I')
Tyr—Leu—Tyr—Gln—Trp—Leu—Gly—Ala—Pro—

10   11   12   13   14   15   16   17   18
Val—Pro—Tyr—Pro—Asp—Pro—Leu—Glu—Pro—

19   20   21   22   23   24   25   26   27
Arg—Arg—Glu—Val—Cys—Glu—Leu—Asn—Pro—

28   29   30   31   32   33   34   35   36
Asp—Cys—Asp—Glu—Leu—Ala—Asp—His—Ile—

37   38   39   40   41   42   43   44   45
Gly—Phe—Gln—Glu—Ala—Tyr—Arg—Arg—Phe—

46   47   48   49
Tyr—Gly—Pro—Val—
```

The object of this invention is to provide a method for the preparation of the desired Glu-OC, and to provide a method for the preparation of human osteocalcin in which the glutamate has been changed to γ-carboxyglutamate with the use of said Glu-OC as a precursor. Another object of this invention is to provide a method for the preparation of purified human osteocalcin which does not contain any other substance arising from the body.

Briefly, the present invention relates to a polypeptide of the following Formula (I):

```
 1    2    3    4    5    6    7    8    9        (I)
X—Tyr—Leu—Tyr—Gln—Trp—Leu—Gly—Ala—Pro—

10   11   12   13   14   15   16   17   18
Val—Pro—Tyr—Pro—Asp—Pro—Leu—Glu—Pro—

19   20   21   22   23   24   25   26   27
Arg—Arg—Glu—Val—Cys—Glu—Leu—Asn—Pro—

28   29   30   31   32   33   34   35   36
Asp—Cys—Asp—Glu—Leu—Ala—Asp—His—Ile—

37   38   39   40   41   42   43   44   45
Gly—Phe—Gln—Glu—Ala—Tyr—Arg—Arg—Phe—

46   47   48   49
Tyr—Gly—Pro—Val—Y
``` in which X is H or H-Lys, and Y is OH or Lys-OH. This invention also relates to purified human osteocalcin which does not contain any other substance arising from the body.

The invention also provides a method for the preparation of a polypeptide which has the acid sequence shown by the Formula (I) in which X is H and Y is OH, by the use of carboxypeptidase B to digest the polypeptide with the amino acid sequence of Formula (I) in which X is H and Y is Lys-OH.

The invention also relates to a method for preparation of the said purified human osteocalcin by the use of vitamin-K-dependent carboxylase to treat the polypeptide of Formula (I) wherein X is H and Y is OH.

The present invention also relates to a precursor of the peptide of the Formula (I), said precursor having the amino acid sequence shown below:

```
 1    2    3    4    5    6    7    8    9        (II)
H-(-Lys—Tyr—Leu—Tyr—Gln—Trp—Leu—Gly—Ala—

10   11   12   13   14   15   16   17   18
Pro—Val—Pro—Tyr—Pro—Asp—Pro—Leu—Glu—

19   20   21   22   23   24   25   26   27
Pro—Arg—Arg—Glu—Val—Cys—Glu—Leu—Asn—

28   29   30   31   32   33   34   35   36
Pro—Asp—Cys—Asp—Glu—Leu—Ala—Asp—His—

37   38   39   40   41   42   43   44   45
Ile—Gly—Phe—Gln—Glu—Ala—Tyr—Arg—Arg—

46   47   48   49   50
Phe—Tyr—Gly—Pro—Val-)$_n$-OH
``` in which n is an integer of 2 or more.

In general, the production of a large amount of peptides of low molecular weight by the techniques of genetic recombination is difficult. The reason therefor seems to be in that peptides of low molecular weight produced inside the host microorganism are readily decomposed by enzymes present in the cells.

We have found that it is possible to obtain the desired polypeptide as a polymerized polypeptide by the method of inserting into a vector multiple copies of the gene coding for the desired polypeptide of Formula (I), i.e. Glu-OC, followed by the culture of recombinants obtained by the transformation of *E. Coli* cells with the recombinant DNA obtained; and that, it is possible to prepare Glu-OC by cleavage of this polymerized polypeptide, and further that by the use of vitamin-K-dependent carboxylase to treat the Glu-OC mentioned above there is obtained the final desired polypeptide, i.e. human osteocalcin.

Figure 2:
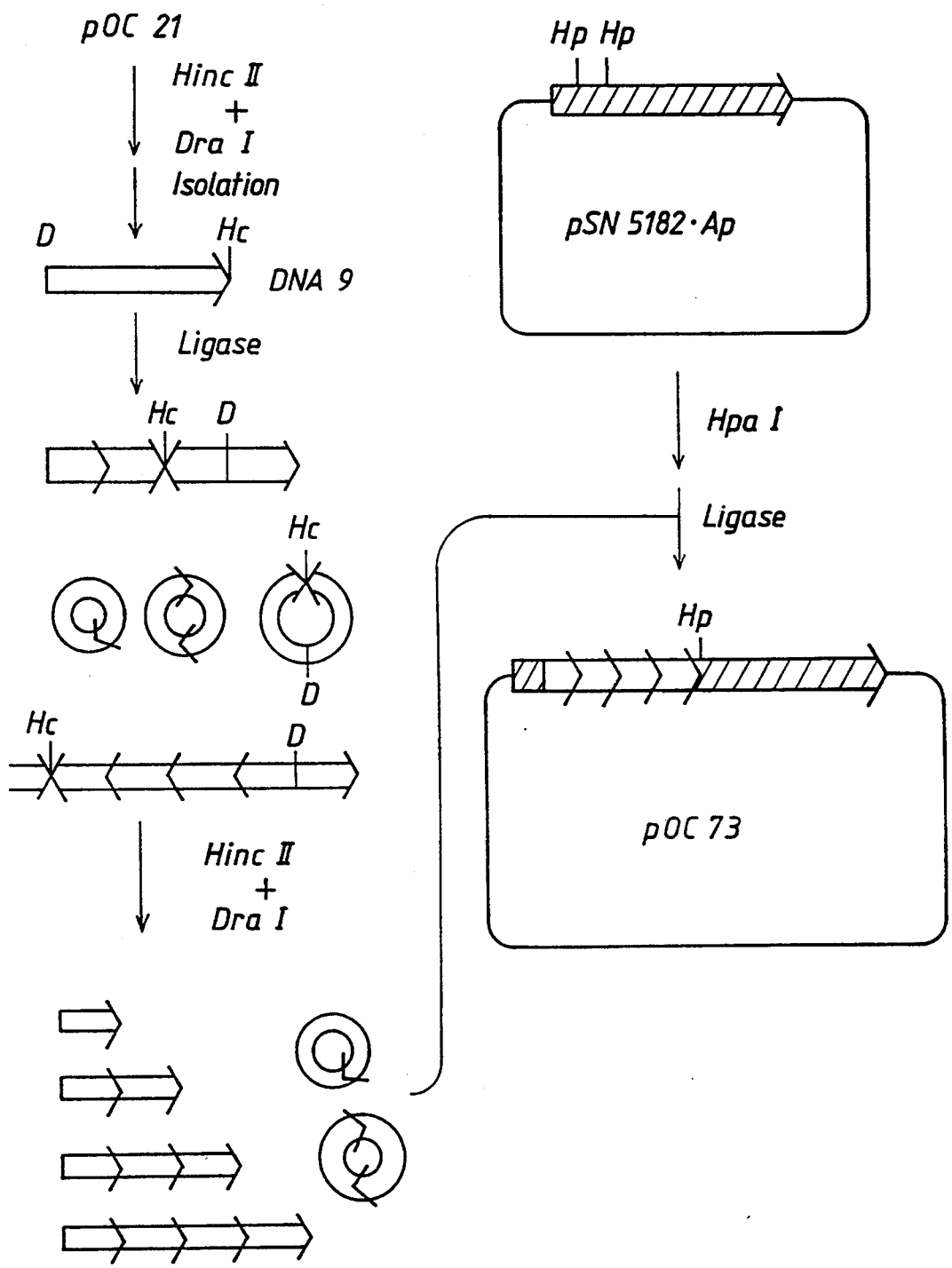
Figure 3:
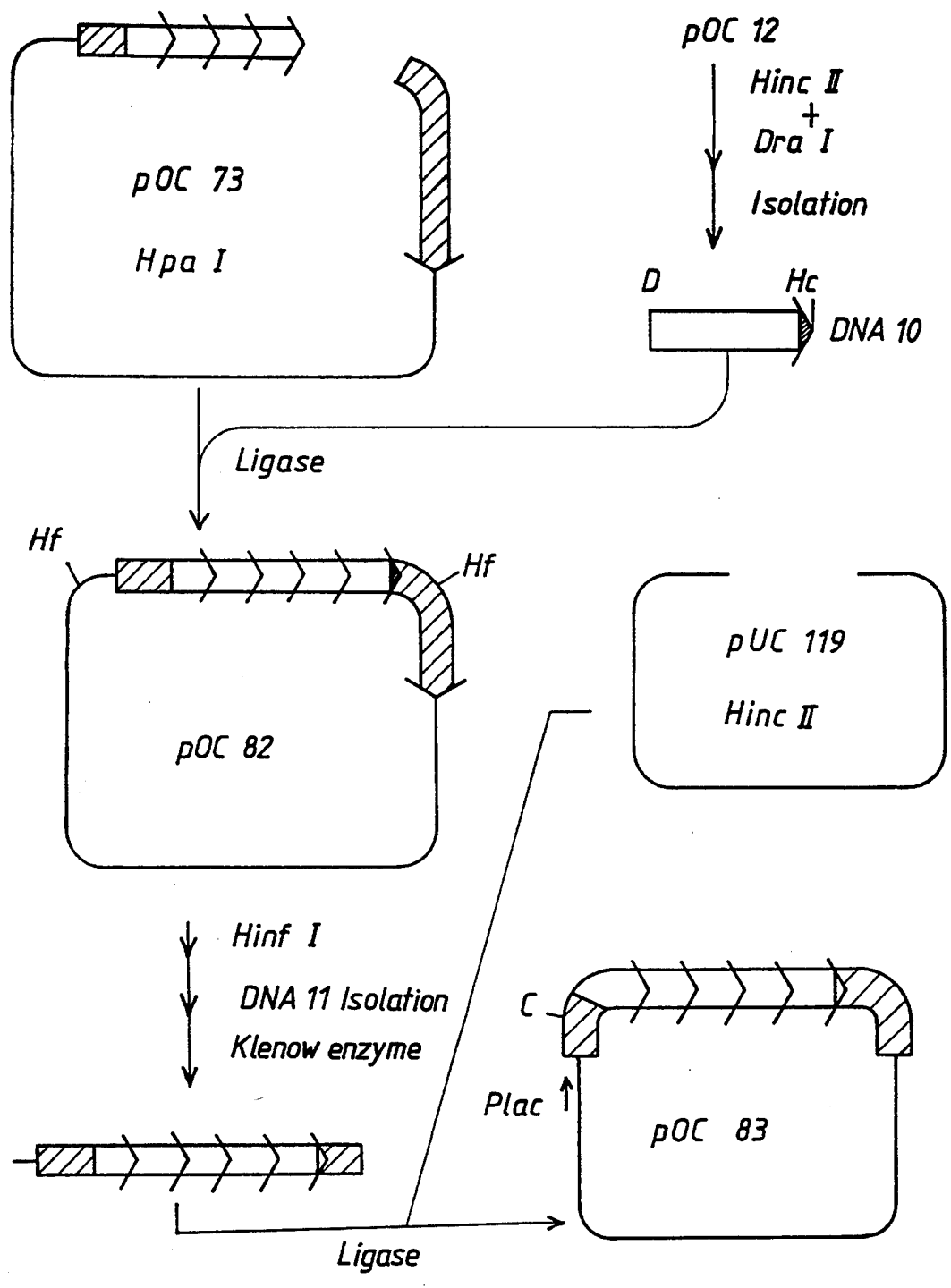

The invention will be explained below in more detail by referring partly to the accompanying drawings wherein are shown the process of preparation (construction), the recognition (cleavage) sites by restriction endonucleases, and the functional maps, of the various plasmids in outline form: FIG. 1 for plasmids pOC12 and pOC21; FIG. 2 for plasmid pOC73; FIG. 3 for plasmids pOC82 and pOC83; and FIG. 4 for plasmid pOC980.

It is possible to prepare the OC precursor by genetic recombination method, for example, as follows.

Step 1. (See FIG. 1)

Synthesis of gene Fragments:

First, DNAs with the structures shown by the following formulae III-VI are synthesized chemically.

(III)
5' AACTTTAAATTCAAATACCTGTACCAGTGGCTG—
GGTGCTCCGGTTCCGTACCCGGACCCGCTGGAA—
CCGCGTCGTGAAGTTTGCGAACTGAAC 3'

(IV)
5' AACGAATTCCTAAACCGGACCGTAGAAACG—
ACGGTAAGCTTCCTGGAAACCGATGTGGTC—
AGCCAGTTCGTCGCAGTCCGGGTTCAGTTC—
GCAAACTTCAC 3'

(V)
5' AACCTTTAAATACCTGTACCAGTGGCTGGGT—
GCTCCGGTTCCGTACCCGGACCCGCTGGA—
ACCGCGTCGTGAAGTTTGCGAACTGAAC 3'

(VI)
5' AACCGGACCGTAGAAACGACGGTAAGCTTCC—
TGGAAACCGATGTGGTCAGCCAGTTCGTC—
GCAGTCCGGGTTCAGTTCGCAAACTTCAC 3' in which A is adenine, T is thymine, G is guanine, and C is cytosine.

The synthesis of these DNAs can be done with an automated DNA synthesizer by solid-phase synthesis with use of the phosphoramidite method.

Next, a double-stranded DNA fragment (hereinafter referred to as gene 7) of the following Formula (VII). is formed by the use of Klenow enzyme by annealing one portion of the DNA shown by Formula (III) (DNA 3 ) to one portion of the DNA shown by Formula IV (DNA 4) so as to Form a double-stranded portion.

(VII)
5' AACTTT|AAATTCAAATACCTGTACCAG—
3' TTGAAA|TTTAAGTTTATGGACATGGTC—

<u>Dra</u> I

TGGCTGGGTGCTCCGGTTCCGTACCCG—
ACCGACCCACGAGGCCAAGGCATGGGC—

GACCCGCTGGAACCGCGTCGTGAAGTT—
CTGGGCGACCTTGGCGCAGCACTTCAA—

TGCGAACTGAACCCGGACTGCGACGAA—
ACGCTTGACTTGGGCCTGACGCTGCTT—

CTGGCTGACCACATCGGTTTCCAGGAA—
GACCGACTGGTGTAGCCAAAGGTCCTT—

GCTTACCGTCGTTTCTACGGTCCGGTT—
CGAATGGCAGCAAAGATGCCAGGCCAA—

TAGGAATTCGTT3'
ATCCTTAAGCAA5' wherein the vertical line labelled DraI is the site of cleavage by the restriction enzyme DraI.

In the same way, a double-stranded DNA fragment (hereinafter referred to as gene 8) of the following Formula (VIII) is formed by the use of Klenow enzyme by annealing one portion of the DNA shown by the Formula (V) (DNA 5) to one portion of the DNA shown by the Formula (VI) (DNA 6) so as to form a double-stranded portion.

(VIII)
5' AACCTTT|AAATACCTGTACCAG—
3' TTGGAAA|TTTATGGACATGGTC—

<u>Dra</u> I

TGGCTGGGTGCTCCGGTTCCGTACCCG—
ACCGACCCACGAGGCCAAGGCATGGGC—

GACCCGCTGGAACCGCGTCGTGAAGTT—
CTGGGCGACCTTGGCGCAGCACTTCAA—

TGCGAACTGAACCCGGACTGCGACGAA—
ACGCTTGACTTGGGCCTGACGCTGCTT—

CTGGCTGACCACATCGGTTTCCAGGAA—
GACCGACTGGTGTAGCCAAAGGTCCTT—

GCTTACCGTCGTTTCTACGGTCCGGTT 3'
CGAATGGCAGCAAAGATGCCAGGCCAA 5'

Step 2 (see FIG. 1)

Construction of a plasmid which contains genes 7 and 8:

Plasmid pUC19 (Takara Shuzo Co., Ltd.) is cleaved with the restriction enzyme HincII, and linked with gene 7 by the use of ligase to form plasmid pOC12. In the same way, HincII is used to cleave pUC19 and gene 8 is ligated to the results to form plasmid pOC21.

Step 3 (see FIG. 2)

Preparation of a plasmid which contains the fused gene pstS-(Glu-OC):

Plasmid pOC21 is cleaved with the restriction enzymes DraI land HincII, and the fragment referred to as DNA 9 below, which codes for the polypeptide of Glu-OC with an added lysine residue at the N terminus [referred to as Lys-(Glu-OC)], is isolated. DNA 9 is ligated with ligase and cleaved with the restriction enzymes DPaI and HincII. In this way, double-stranded DNA is obtained in linear or circular form; it contains multiple copies of DNA 9, all oriented in the same direction and ligated together.

pSN5182 (Magota et al., J. Bacteriol., 157,909 (1984)), which is formed by the integration of 1.5 kb PstI-MluI DNA fragment coding for pstS gene into the PstI-EcoRI sites of pBR322, is cleaved with PstI and EcoRI. The PstI-EcoRI fragment obtained is transferred into pUC19 to form pSN5182.Ap. This pSN5182.Ap is cleaved with restriction enzyme HpaI, and then ligated with the mixture mentioned above in which DNA 9 has been ligated and cleaved. In this way, a plasmid is formed which has (n-1) copies of the Lys-(Glu-OC) genes within pstS gene having the same orientation and reading frame as pstS gene. The n can be any integer of 2 for more; for example, in plasmid pOC73, there are four Lys-(Glu-OC) genes.

Step 4 (see FIG. 3)

Construction of a plasmid that contains Lys-(Glu-OC) genes:

pOC73 contains a gene which codes for a peptide formed from the sequence of 25 amino acids which is the signal peptide, for pstS, the sequence of 31 amino acids which are the N-terminal of mature PstS protein, connected with four copies of Lys-(Glu-OC), and the sequence of 238 amino acids that are the C-terminal of mature PstS protein. The polypeptide which is produced by this gene contains a sequence of 238 amino acids at the C-terminal which is not needed, so it is preferable to remove it.

A DNA fragment (DNA 10) is isolated which codes for Lys-(Glu-OC) by cleavage of pOC12 with the use of HincII and DraI. Also, pOC73 is cleaved with HpaI. By the ligation of these DNAs, plasmid pOC82, which contains five copies of the Lys-(Glu-OC) gene, is formed.

A plasmid is formed which contains (n- 1) copies of the Lys-(Glu-OC) gene by the same method as in step 3. This plasmid is used in this step, which makes it possible to produce a plasmid containing copies of the Lys-(Glu-OC) gene. By the expression of this gene, it is possible to produce a polypeptide with Formula (II) with n copies of Lys-(Glu-OC) connected together.

Now, the case of expression of the gene when there are Five copies: of it will be explained.

The transcription of the fused gene, pstS-[Lys-(Glu-OC)]$_5$, of pOC82 is done under the control of pstS promoter, and is induced with a deficiency of phosphate. With a deficiency of phosphate in the medium, it is difficult to obtain a large amount of product, because growth of the host bacterial cells is poor.

pOC82 is cleaved with the restriction enzyme HinFI, and the DNA fragment (DNA 11) that contains the gene pstS[Lys-(Glu-OC)]$_5$ is isolated. Both ends of the DNA 11 are made blunt with the use of Klenow enzyme, and pOC83 is formed by connection of the resultant DNA with pUCl19 cleaved with HincII. Transcription of the pstS-[Lys-(Glu-OC)]$_5$ gene of pOC83 is done under the control of lac promoter derived from pU119.

Figure 4:
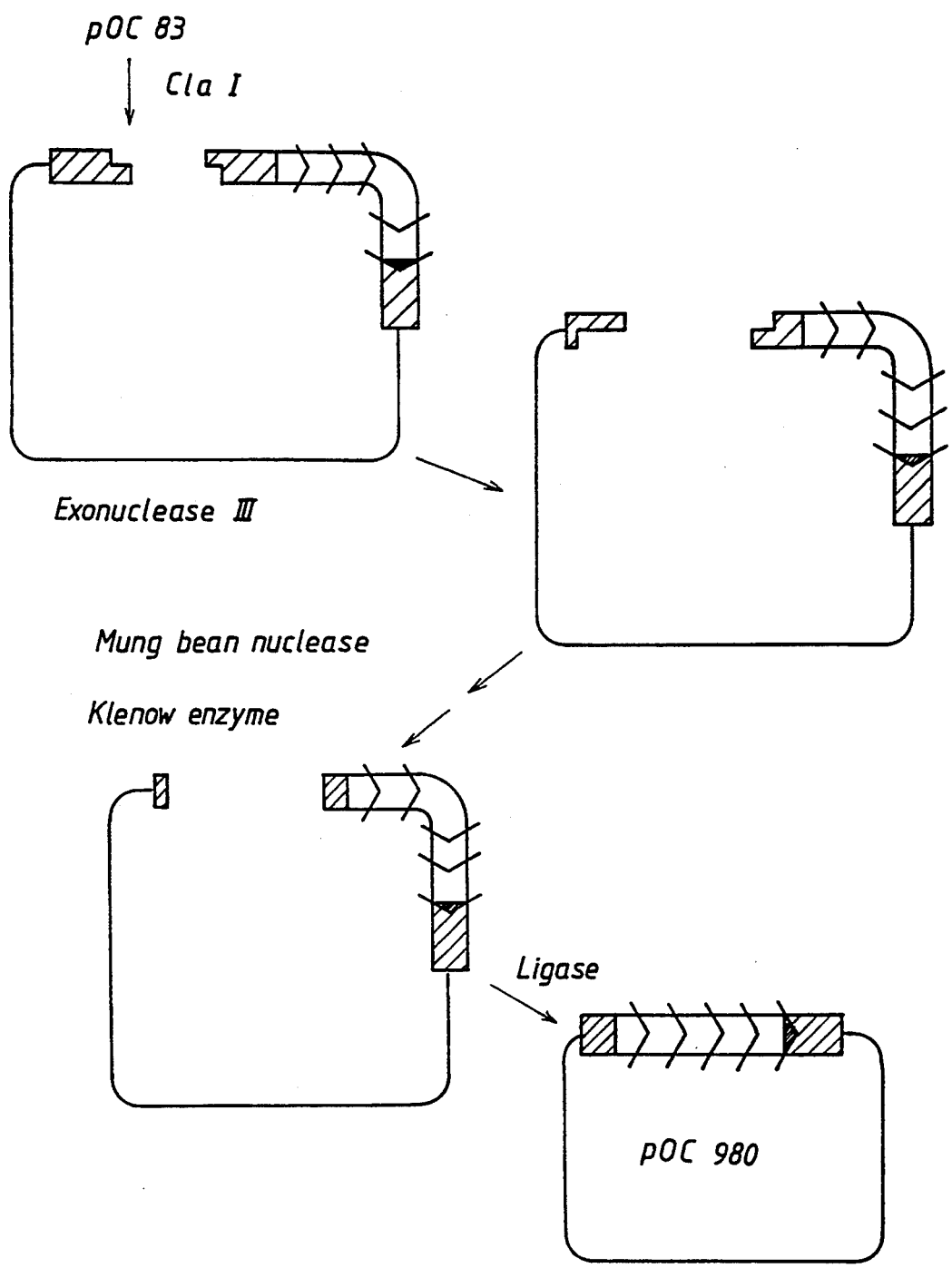

Step 5 (see FIG. 4)

Improvement of Glu-OC productivity:

When $E.\ coli$ cells are used as the host cells for the production of a foreign protein, it is possible to bring about the production of a large amount of the product in the cells by introduction of a mutation in the signal sequence, which makes the product difficult for the cells to decompose [Gentz et al., J. Sacteriol., 170, 2212 (1988)].

At the ClaI site, which is located within a portion which codes for the pOC83 signal sequence, the plasmid is cleaved, and the DNA which codes for the signal sequence is deleted with exonuclease III and mung bean nuclease; the ends are made blunt with Klenow enzyme, and ligase is used to make the DNA circular, giving plasmid pOC980.

$E.\ coli$ cells into which pOC83 had been introduced are cultured, and the whole protein of the bacterial cells is analyzed by use of SDS-polyacrylamide gel electrophoresis and Western blotting with the use of anti-bovine osteocalcin monoclonal antibody. It is not possible to distinguish between the patterns of protein staining of the transformant and that of the host, and by Western blotting, a number of bands of molecular weights lower than that expected are found. When the protein of $E.\ coli$ cells into which pOC980 has been introduced is analyzed in the same way, the main band which appears with protein staining is in the expected position, and there is a single band by Western blotting.

Glu-OC is prepared by the steps described below from a used gene product which is produced in a large amount by use of the procedures of genetic recombination described above, in which used gene product the N-terminal portion of the PstS protein is combined with n copies of Lys-(Glu-OC).

The bacterial cells are disrupted by sonication, and from the insoluble fraction, the particles which contains the desired product that has accumulated in the cells are obtained by sucrose density gradient centrifugation. These particles are dissolved in urea and later hydrolyzed with lysyl endopeptidase, giving a polypeptide with a lysine residue bound to the carboxyl-terminus end of Glu-OC [called (Glu-OC)-Lys below]. The (Glu-OC)-Lys is hydrolyzed with carboxypeptidase B to remove the lysine at the carboxyl end, giving Glu-OC as the product.

As described above, Glu-OC is readily obtained in a large amount by the procedures of genetic recombination. In the method of this invention, the gene of interest is synthesized, linked together with the insertion of the DNA sequence coding for a spacer which can be removed enzymatically, and fused with an appropriate gene. By this method, a large amount of product can be obtained as the product of the used genes in microorganisms, and the product obtained is treated chemically or enzymatically so as to give a monomer.

In this invention, the spacer used is lysine, the monomer is obtained with the use of lysyl endopeptidase, and the spacer is removed with carboxypeptidase B; however, it is possible to use other methods by which the target polypeptide is not cleaved. For example, as cyanogen bromide cleaves on the carboxy side of methionine, a gene that codes for repetitive Glu-OC with a spacer made from Lys-Met is constructed, and after expression of the polymer, monomers are accomplished by the use of cyanogen bromide, and homoserine arising from the methionine by the use of carboxypeptidase A is removed; the desired Glu-OC is then obtained by the removal of lysine by carboxypeptidase B.

It is possible to transform Glu-OC into human osteocalcin by, for example, the use of carboxylase to carboxylate the glutamate. The carboxylase can be, for example, vitamin-K-dependent carboxylase, and it can be prepared, for example, from liver by the method of Girardot and Johnson (Anal. Biochem., 121,315–320, 1982).

It is possible to purify human osteocalcin which is prepared by the use of carboxylase to treat Glu-OC by any of the well-known methods.

One example of a method of preparation is that by which a column that has immobilized on it monoclonal antibody OC4-30 (Takara Shuzo Co., Ltd.) which recognizes human osteocalcin, without recognizing Glu-OC; with this method, purification can be efficient. Or, as human osteocalcin adsorbs onto hydroxyapatite, it is also possible to use column chromatography with hydroxyapatite.

By use of the above methods in a series, it is possible to prepare precursor Glu-OC and the desired purified human osteocalcin which does not contain any other substance arising from the body on an industrial scale, with good efficiency.

This invention will be explained by means of the following examples, but the invention is not to be limited to these specific Examples.

EXAMPLE 1

(1) Preparation of the plasmids pOC12 and pOC21:

In 10 μl of TE buffer (10 mM Tris-HCl, ph 8, containing 1 mM EDTA), 0.25 μg of DNA 3 and also of DNA 4 were dissolved, and the solution was incubated at 65° C. before being allowed to cool to 37° C. To this solution were added dATP, dGTP, dCTP, and TTP, each to the Final concentration of 1 mM. Then 2 U of Klenow enzyme (Takara Shuzo Co., Ltd.) was added to the solution and the mixture was incubated first for 1 hr at 37° C. and then for 15 min at 65° C. to stop the enzyme activity. Separately, 0.1 Bg of pUC19 (Takara Shuzo Co., Ltd.) was cleaved for 1 hr at 37° C. in 5 μl medium-salt buffer (described on p. 453 of *Molecular cloning: A laboratory manual*, T. Maniatis et al., eds., Cold Spring Harbor Laboratory, Cold Spring Harbor (1982)) which contained 5 U of HincII (Takara Shuzo Co., Ltd.). The enzyme was inactivated by the heating of the mixture for 15 min at 65° C., after which this mixture was mixed with the reaction solution of DNA 3 and DNA 4 treated as described above with Klenow .enzyme, and DNA ligation was done with use of a DNA ligation kit (Takara Shuzo Co., Ltd.). This DNA was introduced into JM109 competent cells (Takara Shuzo Co., Ltd.), and the cells were cultured on agar medium which contained ampicillin and 5-bromo-4-chloro-3-indolyl-β-D-galactoside (X-gal). White colonies that grew were selected. These colonies were treated by the alkaline treatment (p. 368 of *Molecular cloning: A laboratory manual*), giving plasmid DNA of pOC12.

By the same method, DNA 5 and DNA 6 were used to obtain pOC21.

The DNA sequences inserted into pOC12 and pOC21 were checked by the dideoxy method (J. Messing, *Methods in Enzymology*, vol. 101, pp. 20–78, 1983). (2) Preparation of plasmid pOC73:

First, 1 μg of pSN5182 was cleaved with 10 U of BamHI and of EcoRI for 2 hr at 37° C. in 10 μl of a high-salt buffer (p. 453 of *Molecular cloning: A laboratory manual*). Then the enzymes were inactivated by being heated for 15 min at 65° C. Separately, 0.1 μg of pUC19 was cleaved with 5 U of BamHI and of EcoRI for 2 hr at 37° C. in 10 μl of a high-salt buffer. Then the enzymes were inactivated by being heated for 15 min at 65° C. The DNAs obtained in this way were ligated for 30 min at 16° C. with use of a DNA ligation kit, and introduced into JM109 competent cells. The cells were cultured on agar medium that contained ampicillin and X-gal and the white colonies that grew were selected. These colonies were treated by the alkaline treatment method, giving pSN5182.Ap.

Next 0.1 μg of pSN5182.Ap was cleaved in 5 μl of TA buffer (as described on p. 421 of O'Farrell et al., *Mol. Gen. Genet.*, 79, 1980) which contained 5 U of HpaI, after which the enzyme was inactivated by being heated at 65° C. for 5 min. Separately, 100 μg of pOC21 was cleaved for 2 hr at 37° C. in 200 μl of medium-salt buffer that contained 100 U of HincII and of DraI. The resulting mixture was treated by electro-phoresis on a 2% agarose gel, which was stained with ethidium bromide, and gel fragments containing DNA that was 150 base pairs (bp) long were obtained, enclosed in a dialysis tube, and electroeluted as described on p. 164 of *Molecular cloning: A laboratory manual*. Phenol treatment was done, and the DNA was obtained by ethanol precipitation. This DNA was ligated with use of a DNA ligation kit, treated with phenol, and precipitated with ethanol. Then the DNA was dissolved in 50 μl of a medium-salt buffer, and allowed to react for 2 hr at 37° C. with 50 U of DraI and of HincII. Then the enzymes were inactivated by treatment at 65° C. for 15 min.

This mixture was ligated with 0.1 μg of the pSN5182. Ap cleaved with HpaI, with use of a DNA ligation kit, and the ligated DNA was introduced into HB101 competent cells (Takara Shuzo Co., Ltd.), which were then cultured. Ampicillin-resistant colonies were selected. From one of these colonies, plasmid pOC73 with four genes for Glu-OC that were arranged in the same orientation as the pstS gene were obtained by alkaline treatment.

(3) Preparation of plasmids pOC82 and pOC83:

First, 5 μg of pOC12 was cleaved for 2 hr at 37° C. in 50 μl of medium-salt buffer containing 20 U of HincII. Agarosegel electrophoresis was done, followed by staining with ethidium bromide. The portion of agarose that stained, which contained. DNA approximately 170 bp long, was sealed in a dialysis tube and electroeluted. Then phenol treatment and ethanol precipitation were done to obtain the DNA.

Separately, 0.1 μg of pOC73 was cleaved for 1 hr at 37° C. in 10 μl of TA buffer containing 5 U of HpaI, and the enzyme was inactivated by heat, after which the DNA obtained here was ligated with the DNA mentioned above by use of a DNA ligation kit. This ligated DNA was introduced into HBO101 competent cells, and ampicillin-resistent colonies were selected. In this way, plasmid pOC82, which contained the fifth Glu-OC gene in the same orientation as four Glu-OC genes was obtained.

Separately, 0 μg of pOC82 was cleaved in 10 μl of TA buffer containing 10 U of HinFI, and the enzyme was then inactivated by being heated for 15 min at 70° C. The mixture was treated by electrophoresis on an agarose gel, and the gel was stained with ethidium bromide; DNA with approximately 1000 bp was obtained by electroelution. This DNA was treated with phenol and obtained by ethanol precipitation. To this DNA was added 10 μl of a solution of dATP, dGT, dCTP, and TTP, each at the concentration of 0.1 mM; the solution was of 10 mM Tris-HCl pH 8, which contained 5 mM $MgC_{12}$. To this mixture, 2 U of Klenow enzyme was added, and the mixture was allowed to react for 5 min at 37° C. Then the enzyme was inactivated by being heated at 65° C. for 15 min.

The resultant mixture was used in ligation with pUC19 which had been cleaved with HincII, and the ligated DNA was introduced into JM109 competent cells. The cells were cultured on agar medium containing ampicillin and X-gal, and the white colonies that grew were selected. From them, plasmid pOC83 was obtained.

(4) Preparation of plasmid pOC980:

First, 2 μg of pOC83 was cleaved for 1 hr at 37° C. in TA buffer containing 10 U of ClaI. This was used to prepare a plasmid from which the signal sequence was deleted, with use of deletion kit for kilo-sequencing (Takara Shuzo Co., Ltd.); the instructions of the manufacturer were followed, except that the reaction times for ExoIII were 15, 30, 45 60, 90 and 105 seconds. This plasmid was introduced into HB101 competent cells, and 80 colonies with ampicillin resistance were selected. These were cultured separately, each in 5 ml of LB-Ap medium (10 g of bacto tryptone, 5 g of yeast extract (both from DiFco), 5 g NaCl, 100 mg/l ampicillin, pH 7.7, and the protein of the bacterial cells was analyzed by electrophoresis on SDS-polyacrylamide gel. One of the cultures with major bands at the position for the molecular weight of 35000–40000 were selected and strain that carried the plasmid pOC980 was obtained. An anti-osteocalcin monoclonal antibody, OC-G2, produced by a hybridoma OC-G2 (FRM BP-2077) obtained from a mouse immunized with bovine osteocalcin was used in Western blotting, by which protein with the molecular weight of 35000–40000 was found to be a polymer of Glu-OC. E. coli cells that carried this plasmid pOC980 were designated E. coli HB101/pOC980, and deposited as FERM BP-2625 with the Fermentation Research Institute, Agency of Industrial Science and Technology.

(5) Production and preparation of polymerized Lys-(Glu-OC) by E. coli HB101/pOC980:

First, cells of E. coli HB101/pOC980 were inoculated into 5 ml of LB-Ap medium, and grown overnight at 37° C. This culture was used to inoculate 200 ml of LB-Ap medium, and the culture was cultivated overnight at 37° C. with aeration with an air pump. This culture fluid was centrifuged for 5 min at $5000 \times g$ and the cells were washed in 20 mM Tris-HCl buffer (pH 8) before being suspended in 10 ml of the same buffer and sonicated for 10 min. The sonicate was centrifuged for 15 min at $10000 \times g$ and the precipitate obtained. Then sucrose was dissolved in 20 mM Tris-HCl buffer (pH 8) to the concentrations of 70% or 50%, and the sucrose solutions were layered in a centrifuge tube. The precipitate obtained above was suspended in 20 mM Tris-HCl buffer (pH 8) and layered onto the top of the sucrose before being centrifuged for 40 min at $20000 \times g$.

The insoluble fraction layered at the interface between the 50% and the 70% sucrose was collected and washed in 20 mM Tris-HCl buffer (pH 8), giving particles that were then suspended in 0.5 ml of 20 mM Tris-HCl buffer (pH 8) containing 8M urea. The suspension was sonicated for 10 min and the soluble fraction was obtained.

(6) preparation of (Glu-OC)-Lys monomer:

Here, 5 μl of the soluble fraction obtained in the above step (5) was mixed with 50 μl of the same buffer, except that it did not contain urea, and to the mixture, 0.01 U of lysyl endopeptidase (Wako Pure Chemical Industries) was added. The mixture was allowed to react for 1 hr at 30° C.

(7) Removal of lysine residue from (Glu-OC)-Lys:

First, 10 g of carboxypeptidase B (Sigma) was added to 100 pl of a solution of the (Glu-OC)-Lys monomers obtained in the above step (6), and the mixture was left for 2 hr at 37° C. Then the reaction was stopped by the addition of 50.1 of 0.1% trifluoroacetate solution. The mixture was separated by high-pressure liquid chromatography with use of a $C_{18}$ reversed-phase column, and Glu-OC was obtained quantitatively.

EXAMPLE 2

(1) Preparation of vitamin-K-dependent carboxylase:

First, 300 g of bovine liver was homogenized in 300 ml of 50 mM 4-morpholinepropanesulphonic acid (MOPS; pH 7.4) containing 1 mM EDTA, 1 mM 2-mercaptoethanol, and 1 mM phenylmethylsulphonyl fluoride (buffer A); the homogenate was centrifuged at $20000 \times g$ for 20 minutes. The supernatant was obtained and centrifuged for 1 hour at $100000 \times g$, and the precipitate was washed in 50 mM MOPS, pH 7.4, containing 0.1M NaCl (buffer B), giving microsomes. The microsomes were suspended in buffer B containing 3-[(3-cholamidopropyl)dimethylammonio]1-propanesulfonate (CHAPS), and the suspension was agitated for 1 hour at 4° C.

CHAPS was added so as to make the final concentration of 1%. This mixture was centrifuged for 1 hour at $200000 \times g$, and the supernatant was obtained. To the supernatant was added ammonium sulfate to 75% saturation, and the mixture was agitated at 4° C. for 30 minutes. Then the mixture was centrifuged for 20 minutes at $10000 \times g$ and the precipitate was suspended in buffer B before being dialyzed against the same buffer, giving solubilized microsomes.

(2) Carboxylation of Glu-OC and purification of human osteocalcin:

First, 1 ng of the Glu-OC obtained by the method of Example 1-(7) was dissolved in 8 ml of a mixture containing 20 mM Tris-HCl, pH 7.5, 150 mM NaCl 5.0M $(NH_4)_2SO_4$, 8 mM $MnCl_2$, 8 mM dithiothreitol, 20 mM $NaHCO_3$, and 0.25 mg/ml vitamin K. To this, 2 ml (about 20 mg of protein/ml) of the solubilized microsomes obtained in Example 2-(1) was added, and carboxylation was allowed to proceed for 16 hours at 17° C. Then the reaction mixture was dialyzed against phosphate-buffered saline (PBS) containing 1. mM $CaCl_2$, and the resultant mixture was put through a Sepharose 4B column (Pharmacia) to which the monoclonal antibody OC4-30 (Takara Shuzo Co., Ltd.), which does not recognize Glu-OC but does recognize native bovine osteocalcin, had been immobilized. Then the column was eluted with PBS containing 0.5% Tween 80, 1 mM $CaCl_2$, and 8M urea. The Fractions that contained human osteocalcin were identified by sandwitch ELISA with the use of the monoclonal antibodies OC4-30 and OC-G4 (Takara Shuzo Co., Ltd.). Then an HCA-column (Mitsui Toatsu) for HPLC that was filled with hydroxy-apatite was used for further purification of the fractions on a density gradient of sodium phosphate buffer (pH 6.8) from 10 to 200 mM. Under these conditions, Glu-OC did not adsorb to the column, and bovine osteocalcin was eluted at about the concentration of 80 mM. The eluate from the OC4-30 column was fractionated, and in the peak that eluted at about the concentration of 80 mM, there was purified human osteocalcin, to Judge from analysis of the amino acid sequence of the first 10 residues from the N-terminus and from the results of ELISA.

As explained in detail above, it is possible to construct a gene which codes for the polymerized precursor of human osteocalcin by use of this invention. By the microorganisms transformed with plasmids which carry this gene, it is possible to produce this polymer efficiently. By the enzymatic removal of the spacer in the polymer, it is possible to prepare the precursor of human osteocalcin efficiently, and it is possible to prepare purified human osteocalcin that is suitable for use in pharmaceutical preparations with efficiency from the said precursor of human osteocalcin by the use of enzymatic treatment.

What we claim is:

1. A method for production of Glu-OC polypeptide of the formula (I) in which X is H and Y is OH, comprising the steps of:

| 1 | 2 | 3 | 4 | 5 | 6 | 7 | 8 | 9 |
|---|---|---|---|---|---|---|---|---|
| X— | Tyr— | Leu— | Tyr— | Gln— | Trp— | Leu— | Gly— | Ala—Pro— |

| 10 | 11 | 12 | 13 | 14 | 15 | 16 | 17 | 18 |
|---|---|---|---|---|---|---|---|---|
| Val— | Pro— | Tyr— | Pro— | Asp— | Pro— | Leu— | Glu— | Pro— |

| 19 | 20 | 21 | 22 | 23 | 24 | 25 | 26 | 27 |
|---|---|---|---|---|---|---|---|---|
| Arg— | Arg— | Glu— | Val— | Cys— | Glu— | Leu— | Asn— | Pro— |

| 28 | 29 | 30 | 31 | 32 | 33 | 34 | 35 | 36 |
|---|---|---|---|---|---|---|---|---|
| Asp— | Cys— | Asp— | Glu— | Leu— | Ala— | Asp— | His— | Ile |

| 37 | 38 | 39 | 40 | 41 | 42 | 43 | 44 | 45 |
|---|---|---|---|---|---|---|---|---|
| Gly— | Phe— | Gln— | Glu— | Ala— | Tyr— | Arg— | Arg— | Phe— |

| 46 | 47 | 48 | 49 |
|---|---|---|---|
| Tyr— | Gly— | Pro— | Val—Y |

(wherein X is H or Lys, and Y is OH or Lys)

(a) producing a polymerized (Lys-Glu-OC) polypeptide of the formula (I) in which X is Lys and Y is OH, by a recombinant *Escherichia coli* transformed with a gene coding for the said polymerized (Lys-Glu-OC) polypeptide, (b) cleaving the polymerized (Lys-Glu-OC) polypeptide obtained by step (a) with lysyl endopeptidase to form (Glu-OC-Lys) polypeptide of the formula (I) in which X is H and Y is Lys and (c) cleaving the (Glu-OC-Lys) polypeptide obtained by step (b) with carboxypeptidase B to form Glu-OC polypeptide.

* * * * *